United States Patent [19]

Strohmaier et al.

[11] Patent Number: 4,519,780
[45] Date of Patent: May 28, 1985

[54] DENTAL HANDPIECE

[75] Inventors: Ernst Strohmaier, Bad Schussenried; Heinrich Reich, Hochdorf; Bernd Wagner, Biberach, all of Fed. Rep. of Germany

[73] Assignee: Kaltenbach & Voigt GmbH & Co., Biberach, Fed. Rep. of Germany

[21] Appl. No.: 477,213

[22] Filed: Mar. 21, 1983

[30] Foreign Application Priority Data

Apr. 23, 1982 [DE] Fed. Rep. of Germany ....... 3215210

[51] Int. Cl.³ ............................................. A61C 1/00
[52] U.S. Cl. ..................................... 433/29; 433/126
[58] Field of Search ............... 433/29, 126, 85, 114, 433/131, 132, 105, 103; 350/96.21, 96.15

[56] References Cited

U.S. PATENT DOCUMENTS

| 4,398,885 | 8/1983 | Loge et al. | 433/126 |
| 4,403,956 | 9/1983 | Nakanishi | 433/126 |
| 4,406,621 | 9/1983 | Bailey | 433/126 |

FOREIGN PATENT DOCUMENTS 3132995 3/1983 Fed. Rep. of Germany ........ 433/29

Primary Examiner—Gene Mancene
Assistant Examiner—John G. Weiss
Attorney, Agent, or Firm—Scully, Scott, Murphy & Presser

[57] ABSTRACT

There is disclosed a dental handpiece which mounts a dental implement at one end thereof, drive means provided in the handpiece to operate the dental implement, a connection piece pivotally connected to an opposite end of the handpiece so as to permit relative rotation between the handpiece and the connection piece, means provided in the connection piece to enable a handpiece-supply line to be coupled therewith, a light source, and a light guide having a light-receiving end arranged to receive light from the light source and a light-emitting end arranged to direct light to a treatment region adjacent to the dental implement. In order to avoid any impediment to operation of the handpiece caused by the presence of the light guide, the light guide is arranged to extend within the handpiece and the connection piece. Further, the light guide is transversely divided into first and second guide portions in the region of the connection between the handpiece and the connection piece, and the first guide portion extends within the connection piece and terminates in the connection region between the handpiece and the connection piece, and the second guide portion extends from this connection region within the handpiece towards the implement end. To provide for transmission of light between the first and second guide portions, despite relative rotation taking place between the handpiece and the connection piece, a pair of light transmitting rings are provided, one being arranged in the connection piece to co-operate with the first guide portion and the other being arranged in the handpiece to co-operate with the second guide portion.

29 Claims, 18 Drawing Figures

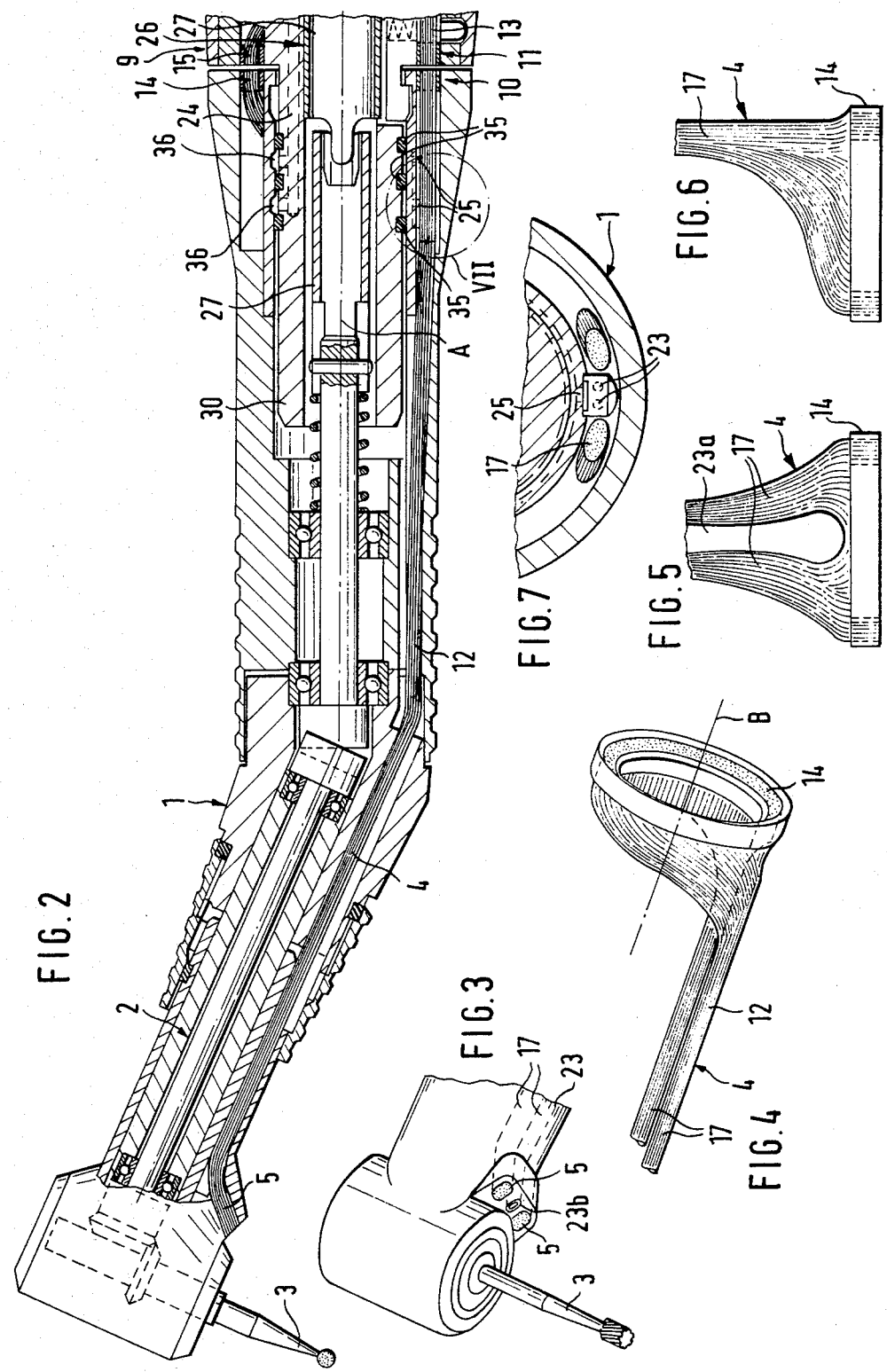

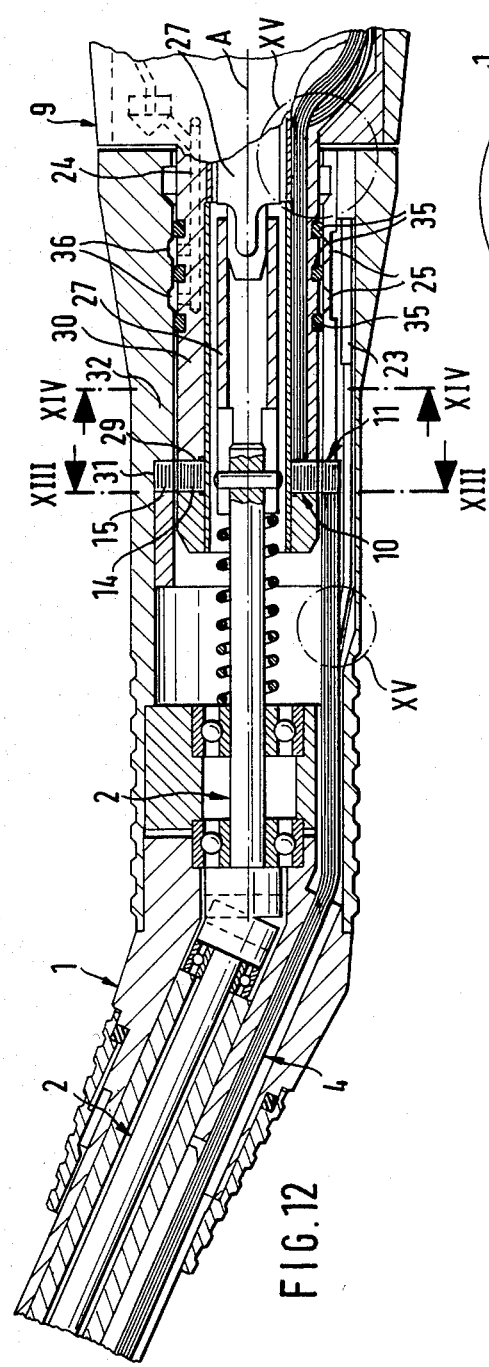
FIG.12
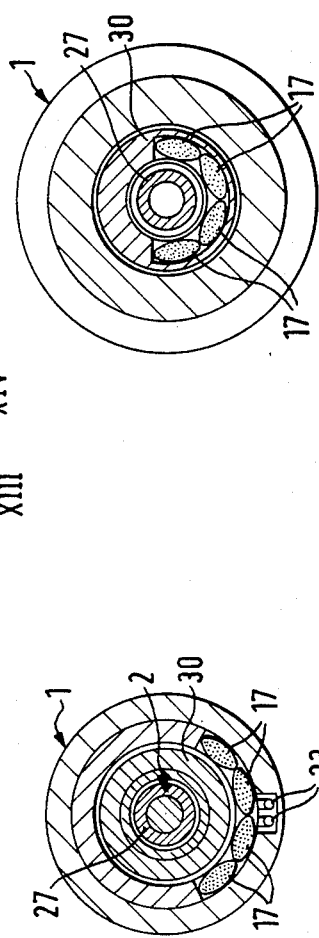
FIG.14
FIG.13
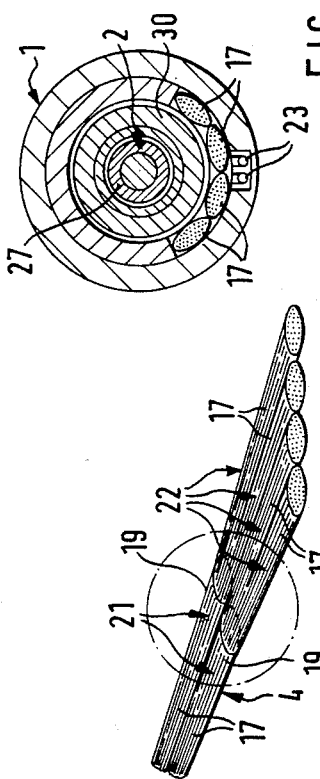
FIG.15

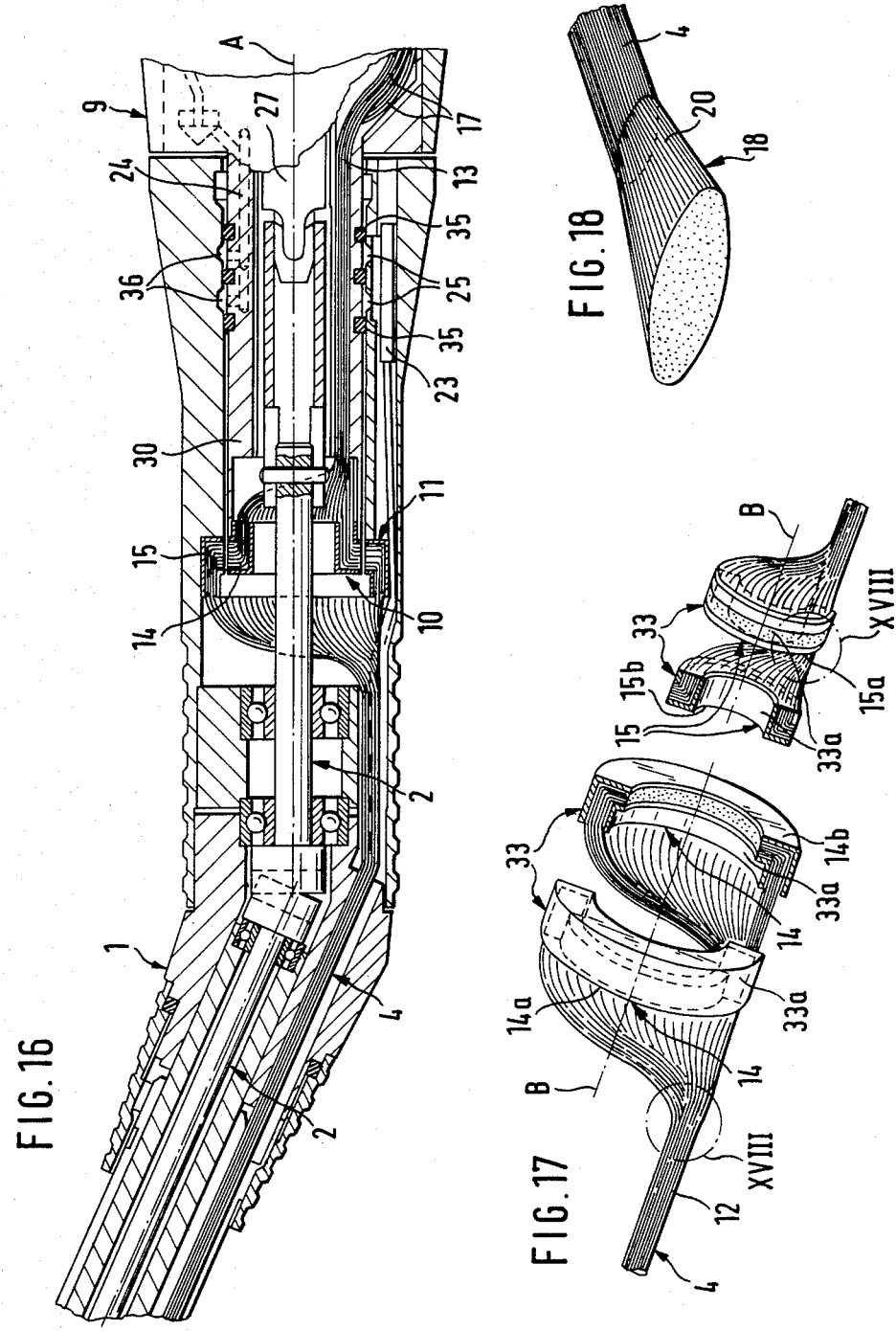

DENTAL HANDPIECE

This invention relates to a straight or angled dental handpiece comprising means provided at one end of the handpiece to mount a dental implement, a drive means provided in the handpiece to operate the dental implement, a connection piece pivotally connected to an opposite end of the handpiece so as to permit relative rotation between the handpiece and the connection piece, means provided in the connection piece to enable a handpiece-supply line to be coupled therewith, a light source, and a light guide having a light-receiving end arranged to receive light from the light source and a light-emitting end arranged to direct light to a treatment region adjacent to the dental implement.

BRIEF DESCRIPTION OF THE PRIOR ART

A handpiece of the above general type is known from DE-GM No. 69 40 204. In this known handpiece a fibre-optic light guide runs inside a flexible hose which also contains media lines for water and/or air, passing from a supply part which is connected with the connection piece externally along the handpiece and the connection piece as far as the tool-side end of the handpiece. The mutual rotatability of the handpiece in respect of the connection piece plus supply part is achieved through the fact that the hose has a certain overlength which can be only slight on account of the relatively small dimensions of the handpiece. However, this slight hose overlength restricts said mutual rotatability. Furthermore, the hose, which passes on the outside of the handpiece and the connection piece, makes it very difficult to grasp and hold the handpiece and to use it on the patient.

OBJECT OF THE INVENTION

The invention has been developed with a view to provide a dental handpiece of the general type referred to above, in which there is no impediment to relative rotation taking place between the connection piece and the handpiece in service, despite the presence of a light guide arranged to direct light to the dental treatment region.

According to the invention there is provided a dental handpiece comprising means provided at one end of the handpiece to mount a dental implement, drive means provided in the handpiece to operate the dental implement when the latter is mounted on the handpiece, a connection piece pivotally connected to a second end of the handpiece which is remote from said one end thereof so as to permit relative rotation between the handpiece and the connection piece, means provided in the connection piece to enable a hanpiece-supply line to be coupled therewith, a light source, and a light guide having a light-receiving end arranged to receive light from said light source and a light-emitting end arranged to direct light to a treatment region adjacent to the dental implement, wherein:
  (a) the light guide arranged to extend within the handpiece and the connection piece;
  (b) the light guide is transversely divided into separate first and second guide portions in the region of the connection between the handpiece and the connection piece;
  (c) the first guide portion extends within the connection piece and has a first end which provides said light-receiving end of the light guide and a second end which is located in said connection region, and the second guide portion extends within the handpiece and has a first end which is located in said connection region and a second end which provides said light-emitting end of the light guide; and
  (d) a pair of annular light-transmitting arrangements are provided one at each of said second end of the first guide portion and said first end of said second guide portion, said annular light arrangements providing for transmission of light therebetween whereby light admitted to said first end of the first guide portion is transmitted via the first guide portion, said pair of annular arrangements, and said second guide portion to be emitted from the second end thereof, and one of said annular arrangements being provided in the handpiece and the other being provided in the connection piece.

A dental handpiece according to the invention has the advantage that the light guide e.g. a fibre-optic light guide, is arranged inside the handpiece so that it cannot cause any impediment to operation and manipulation of the handpiece. Furthermore, in that the light guide is transversely divided in the connection region between the handpiece and the connection piece, there is no impediment to relative rotation between these parts. The provision of the pair of annular light transmitting arrangements allows optimum light efficiency in the transmission of light from the first light guide portion in the connection piece to the second light guide portion in the handpiece, even while relative rotation of the handpiece and the connection piece takes place.

Embodiments of dental handpiece according to the invention will now be described in detail, by way of example only, with reference to the accompanying drawings.

BRIEF DESCRIPTION OF THE DRAWINGS

FIG. 2 shows, on a larger scale, a sectional view of the handpiece shown in FIG. 1;

FIG. 3 is a diagrammatical representation of the tool-side end part of the handpiece shown in FIG. 2;

FIG. 4 is a diagrammatic representation of the handpiece end remote from the dental tool, showing a fibre-optic light guide section which is arranged in the handpiece;

FIG. 5 is an inverted-plan view of the end of the fibre-optic light guide of FIG. 4;

FIG. 6 is a side view of the end of the fibre-optic light guide of FIG. 4;

FIG. 7 shows on a larger scale a sectional drawing of the detail VII characterised in FIG. 2 with a circle;

FIG. 12 is a sectional view of the handpiece in a further form which is modified in respect of FIG. 2;

FIG. 13 is a section in accordance with line XIII—XIII in FIG. 12;

FIG. 14 is a section in accordance with line XIV—XIV in FIG. 12;

FIG. 15 is a diagrammatic representation of the two details XV of the fibre-optic light guide which are characterised in FIG. 12 with a circle respectively;

FIG. 16 is a sectional view of the handpiece in a further form which is modified in respect of FIG. 2;

FIG. 17 is a diagrammatic representation of the adjacent ends of the fibre-optic guide sections which are arranged in the handpiece and in the connection piece respectively according to FIG. 16; and FIG. 18 shows on a larger scale a diagrammatic representation of the two details XVIII of the fibre-optic light guide sections which are characterised in FIG. 17 with a circle respectively.

DESCRIPTION OF PREFERRED EMBODIMENTS

Figure 1:
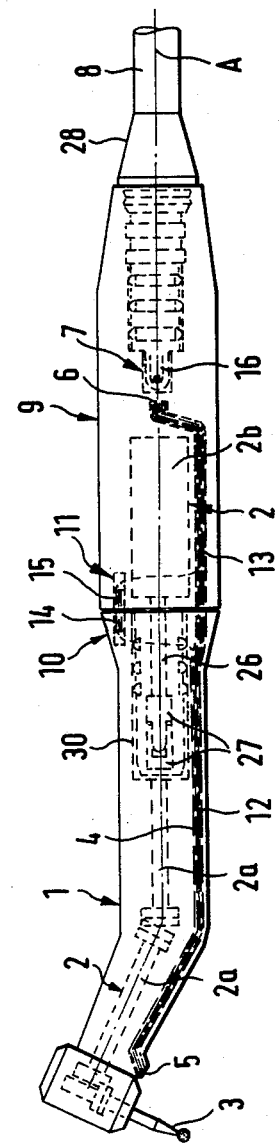
FIG. 1 is a sectional view of a schematic representation of a dental handpiece with an attached connection piece and supply part.
Figure 8:
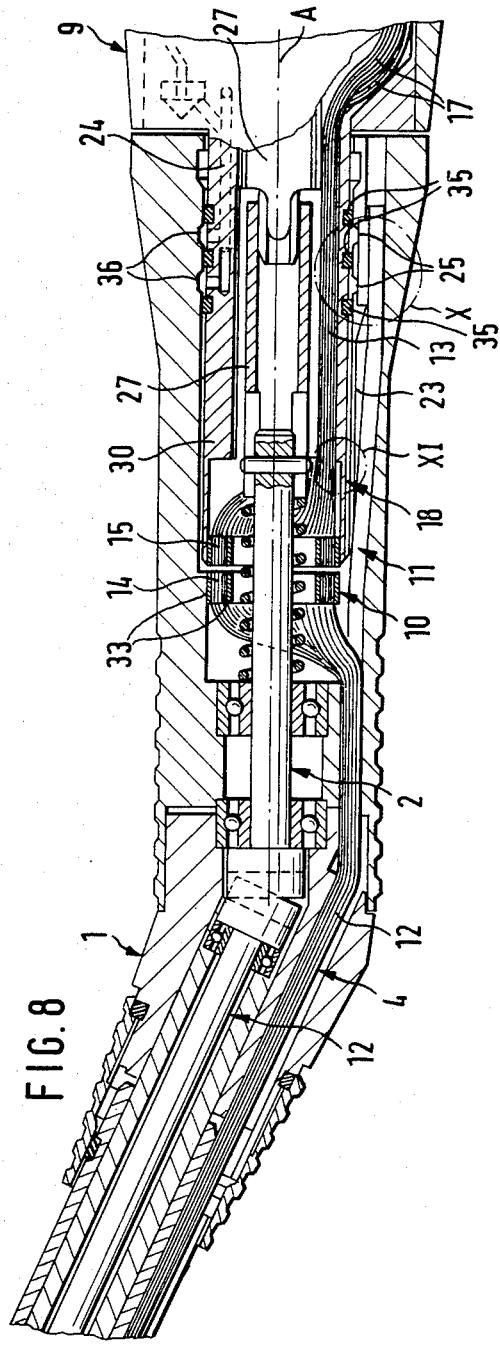
FIG. 8 is a sectional drawing of the handpiece in a form which is modified in respect of FIG. 2.

Referring now to FIGS. 1 to 7, a dental handpiece 1 has driving means 2 arranged therein for operating a dental implement, such as a dental tool or drill 3. In the illustrated embodiment, the driving means 2 comprises mechanical driving elements, namely a driving shaft 2a with a driving motor 2b co-ordinated or coupled therewith to rotate the tool 3 which is provided at one end of the handpiece 1. The driving means 2 may also be pneumatic driving elements (not shown), for example, a compressed air line which leads to a turbine which is arranged in the tool-side end portion of the handpiece 1 and which drives the tool 3. The driving motor 2b, which can be seen in FIG. 1, can be formed, for example, by an electric motor, a fluid motor, or a rotating piston air motor.

The handpiece 1 is also provided with a fibre-optic light guide 4 of which an end 5 which is located at the tool-side end of the handpiece is directed towards the area of the tool 3 i.e. to a treatment region adjacent to the tool, and of which a light-receiving end 6 (which is remote from the tool 3) faces an electrically energisable light source 7 which is formed by an incandescent lamp 16. At its end which is remote from the tool the handpiece 1 is advantageously detachably connected with a connection piece 9 in such a way as to be relatively rotatable about a common axis A, which said connection piece 9 is connected to a handpiece-supply tube or hose 8. The fibre-optic light guide 4 extends with its light-receiving end 6 into the connection piece 9.

It can also be seen from the drawing that the fibre-optic light guide 4 is arranged inside the handpiece 1 and the connection piece 9 and is divided transversely into first and second separated light guide portions 13 and 12 respectively. In a transition connection region between the handpiece 1 and the connection piece 9. The first guide portion extends within the connection piece 9 and has a first end which provides the light-receiving end of the light guide 4 and a second end which is located in the connection region between the handpiece 1 and the connection piece 9. The second guide portion 12 extends within the handpiece 1 and has a first end which is located in the connection region between the handpiece 1 and the connection piece 9 and a second end adjacent the dental tool 3 which provides the light-emitting end of the light guide 4.

A pair of annular light-transmitting arrangements are provided, one being arranged at the second end of the first guide portion 13 and the other being arranged at the first end of the second guide portion 12 i.e. both annular light-transmitting arrangements are provided within the connection region between the handpiece 1 and the connection piece 9. The annular light arrangements provide for transmission of light therebetween, whereby light admitted to the first end of the first guide portion 13 is transmitted via the first guide portion 13, the pairs of annular arrangements, and the second guide portion 12 to be emitted from the second end thereof in order to illuminate the dental treatment region. One of the annular arrangements is provided within the handpiece 1, and the other is provided within the connection piece 9.

The pair of annular light transmitting arrangements are provided by a pair of facing, closely spaced light transmitting rings 14 and 15 which co-operate with the adjacent ends 10, 11 of the fibre-optic light guide portions 12 and 13 which are separated from each other within the connection region between the handpiece 1 and the connection piece 9.

In the embodiments according to FIGS. 1 to 11, the arrangement is such that the light transmitting rings 14, 15 have essentially the same diameter and are arranged with their radially extending annular surfaces adjacent to and facing one another, whereas the embodiments according to FIGS. 12 to 18 have light transmitting rings 14 and 15 of unequal diameters and arranged concentrically one within the other.

For improved light efficiency, both or one of the two fibre-optic light guide portions 12, 13 can be formed by several, in the case represented, by two or four respectively, fibre-optic light guide bundles (skeins) 17 which run side-by-side.

Figure 9:
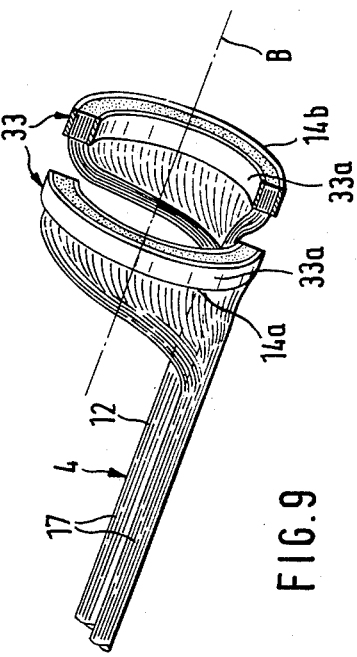
FIG. 9 shows a diagrammatic representation of the end, which is remote from the dental tool, of the fibre-optic light guide section which is arranged in the handpiece according to FIG. 8.

Likewise in order to achieve optimum light efficiency, and also for assembling purposes, the light transmitting rings 14, 15 are sub-divided into several—in the case of FIGS. 9 and 17 into two part-annular sections 14a; 15a, 15b, with at least one fibre-optic light guide bundle 17 co-operating with each annular section (14a, 14b; 15a,15b).

In the embodiment according to FIGS. 4 to 6, the ends of the fibre-optic light guide bundles 17 which run severally side-by-side co-operate with a one-piece light transmitting ring 14, 15 respectively.

Figure 11:
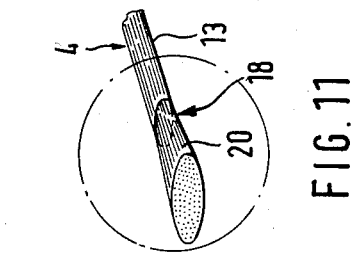
FIG. 11 shows a diagrammatic representation of the detail XI of the fibre-optic light guide which is characterised in FIG. 8 with a circle.

As, for example, FIGS. 11 and 18 show particularly clearly, a further embodiment which is advantageous in respect of optimum light conductance and light transmission consists in that an end area 18 of the fibre-optic light guide portions 12, 13 which adjoins the light transmitting ring 14, 15 is formed with a conical enlargement towards the light transmitting ring 14 and 15 respectively as a receiving- or emitting funnel 19, 20. In order to maintain the funnel shape, the area 18 can advantageously be fixed with an adhesive, for example a synthetic resin adhesive.

As is shown particularly in FIG. 15, a further advantageous embodiment is characterised in that an area 21 which precedes the transition of the fibre-optic light guide 4 and of the fibre-optic light guide bundle 17 respectively into several fibre-optic light guide bundles is formed with a conical enlargement towards the transition as an emitting funnel 19. Similarly, the area 22 of the beginning of the fibre-optic light guide bundles 17 is also formed with a conical enlargement from the transition from the fibre-optic light guide 4.

Figure 10:
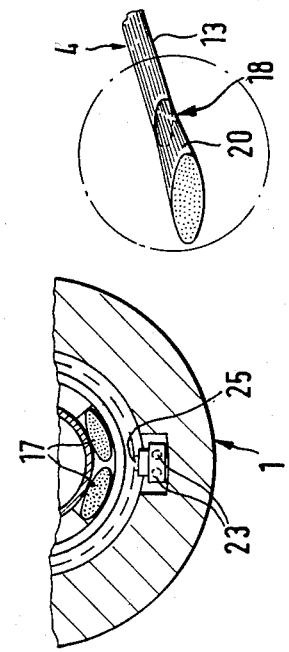
FIG. 10 shows on a larger scale a sectional view of the detail X which is characterised in FIG. 8 with a circle.

It is clear more particularly from FIGS. 7, 10 and 13 that a further advantageous embodiment consists in that one or more fluid media delivery lines 23 which are supplied from the connection piece 9 run alongside of the fibre-optic light guide 4 or alongside of or between several fibre-optic light guide bundles 17 within the handpiece 1. There are coordinated with the media lines 23 which are arranged in the handpiece 1 feed-media supply lines 24 which are provided in the connection piece 9. Communication is established between lines 23 and 24 by media line-transitions 25 between handpiece 1 and connection piece 9 which are effective during relative rotation of these parts (1, 9) about the axis (A) and in each position of rotation, which is achieved with the aid of a centre spigot 30, known per se, of the connection piece 9, interacting with annular seals 35 and annular channels 36. FIG. 5 shows an interspace 23a between two fibre-optic light guide bundles 17 wherein are arranged the media delivery lines 23 which, in accordance with FIG. 5, discharge at their tool end 23b in a direction towards the area of the tool 3.

It is evident from FIG. 1 that there is arranged in the connection piece 9 a driving motor 2b which forms part of the driving means 2 and which engages, via a drive shaft 26 by means of a driving element 27, with a driving shaft 2a (which also forms part of the driving means 2) and which is carried inside the handpiece.

FIG. 1 also shows that the connection piece 9 is connected at its end which is remote from the tool with the tool end of a supply part 28 which is provided with the supply hose 8 and which contains supply media lines which are co-ordinated with the supply media lines 24. At the tool end of supply part 28 there is arranged the light source 7 with which electrical current supply lines (not shown), which are arranged in the supply hose 8 and in the supply part 28, are coordinated.

In the embodiment according to FIGS. 12 to 15 the light transmitting rings 14, 15 are component parts which are separate from both fibre-optic light guide portions 12, 13; the adjacent ends 10, 11 of the fibre-optic light guide portions 14, 15 with their filaments from a butt joint with the light transmitting rings. The arrangement is such that one of the light transmitting rings 14, 15 (which are arranged concentrically one inside the other) is arranged in an outer annular groove 29 of the centre spigot 30 of the connection piece 9 which is inserted into the end of the handpiece 1 which is remote from the tool, and the other light transmitting ring is arranged in an inner annular groove 31 of the wall section 32 of the handpiece 1 which receives the centre spigot 30.

In this embodiment the light transmitting rings 14, 15 advantageously consist of solid material; glass, plastics material, or the like, is generally suitable as material.

In the embodiments according to FIGS. 2 to 11 and 16 to 18 which are definitely more advantageous with regard to optimum light light efficiency with light transmission, the light transmitting rings 14, 15 consist of the same material as the fibre-optic light guide portions 12, 13; the material of the fibre-optic light guide portions 12, 13 and of the light transmitting rings 14, 15 thus blend together. Moreover, the embodiment is such that the fibre-optic light guide portions 12, 13 consist of a bundle of fibre-optic light guide filaments which in the area of the adjacent ends 10, 11 of the fibre-optic light guide portions are the most part bent out of the bundle of the fibre-optic light guide portion, to form the light transmitting rings 14, 15.

In the embodiments according to FIGS. 2 to 11, the ends of the fibre-optical light guide filaments at the adjacent ends 10, 11 of the fibre-optic light guide portions 12, 13 run essentially in parallel with the axis (B) of the light transmitting ring 14, 15. These ends of the fibre-optic light guide filaments are directed towards the other of the two adjacent light transmitting rings 14, 15.

In contrast, in the embodiment according to FIGS. 16 to 18 the design is such that the ends of the fibre-optic light guide filaments at the adjacent ends 10, 11 of the fibre-optic light guide portions 12, 13 are bent in a direction which is transverse to the axix (B) of the light transmitting ring 14 and 15 respectively and are directed towards the other of the light transmitting rings 14, 15 which lie one inside the other.

The end areas of the fibre-optic light guide filaments which form the light transmitting rings 14, 15 are fixed in their position. Thus in the embodiment according to FIGS. 2 to 7 the end areas of the fibre-optic light guide filaments are treated with an adhesive, for example, synthetic resin, for fixing purposes, whereas in the embodiments according to FIGS. 8 to 11 and 16 to 18 the end areas of the fibre-optic light guide filaments are covered for fixing on the outside and on the inside of the light transmitting ring with an annular band 33 respectively which leaves open the ends of the fibre-optic light guide filaments. Corresponding to the two part annular sections 14a, 14b, 15a, 15b, the annular bands 33 are formed by two semicircular ring halves 33a respectively. The annular bands 33 can advantageously consist of light-proof material, for example, metal, plastics material, or the like. The incandescent lamp 16 can be formed by a filament bulb; or any other electrically energisable light may be provided.

We claim:

1. A dental handpiece comprising means provided at one end of the handpiece to mount a dental implement, drive means provided in the handpiece to operate the dental implement when the latter is mounted on the handpiece, a connection piece pivotally connected to a second end of the handpiece which is remote from said one end thereof so as to permit relative rotation between the handpiece and the connection piece, means provided in the connection piece to enable a handpiece-supply line to be coupled therewith, a light source, and a light guide having a light-receiving end arranged to receive light from said light source and a light-emitting end arranged to direct light to a treatment region adjacent to the dental implement, wherein:

(a) the light guide is arranged to extend within the handpiece and the connection piece;
(b) the light guide is transversely divided into separate first and second guide portions in the region of the connection between the handpiece and the connection piece;
(c) the first guide portion extends within the connection piece and has a first end which provides said light-receiving end of the light guide and a second end which is located in said connection region, and the second guide portion extends within the handpiece and has a first end which is located in said connection region and a second end which provides said light-emitting end of the light guide; and
(d) a pair of annular light-transmitting arrangements are provided one at each of said second end of the first guide portion and said first end of the second guide portion, said annular light arrangements providing for transmission of light therebetween whereby light admitted to said first end of the first guide portion is transmitted via the first guide portion, said pair of annular arrangements, and said second guide portion to be emitted from the second end thereof, and one of said annular arrangements being provided in the handpiece and the other of said annular arrangements being provided in the connection piece.

2. A dental handpiece according to claim 1, in which said light source is an electrically energisable light.

3. A dental handpiece according to claim 1, in which said annular light transmitting arrangements have substantially the same diameter and are arranged with radially extending annular surfaces facing each other.

4. A dental handpiece according to claim 1, in which said annular light transmitting arrangements have different diameters and are arranged concentrically one within the other.

5. A dental handpiece according to claim 1, in which the light guide is a fibre optic light guide having a plurality of light guide bundles extendingg side by side.

6. A dental handpiece according to claim 5, in which each of said annular light transmitting arrangements is sub-divided into a plurality of part-annular portions.

7. A dental handpiece according to claim 6, in which each of said light guide bundles is arranged to co-operate with a respective one of said part-annular portions.

8. A dental handpiece according to claim 5, in which each of said annular light transmitting arrangements co-operates with the adjacent ends of light guide bundles of the respective guide portion.

9. A dental handpiece according to claim 1, in which said second end of the first guide portion and said first end of the second guide portion are connected to the respective annular arrangements via conical enlargements which form light-emitting and light-receiving funnels respectively.

10. A dental handpiece according to claim 5, including conical enlargements provided on said first and second guide portions, in regions preceding their merging into respective pluralities of light guide bundles, to form light-emitting funnels.

11. A dental handpiece according to claim 10, in which each of said guide portions merges into a respective plurality of light guide bundles via a respective conical enlargement.

12. A dental handpiece according to claim 5, including a fluid medium delivery line extending within the handpiece alongside said light guide bundles.

13. A dental handpiece according to claim 12, including a fluid medium supply line arranged in the connection piece to co-operate with the fluid medium delivery line in the handpiece.

14. A dental handpiece according to claim 13, including communication means arranged in the connection region between the handpiece and the connection piece to provide communication between said fluid medium supply line and said fluid medium delivery line during relative rotation and in any rotational position of the handpiece and the connection piece.

15. A dental handpiece according to claim 14, including a drive motor arranged in said connection piece, and a drive train for operating the dental implement coupled with said drive motor and extending within the connection piece and the handpiece.

16. A dental handpiece according to claim 13, including a supply component having said handpiece-supply line coupled therewith and connected at one end to an end of said connection piece remote from the handpiece, and a fluid medium line provided in said handpiece-supply line to co-operate with said fluid medium supply line, said light source being provided at said one end of the supply component.

17. A dental handpiece according to claim 1, in which said annular light transmitting arrangements comprise component parts which are separate from said first and second guide portions, and said second end of the first guide portion and said first end of the second guide portion form butt joints with the respective annular arrangements.

18. A dental handpiece according to claim 4, including a central spigot provided on said connection piece to be received by said second end of the handpiece, an annular groove provided on the exterior of said spigot to receive one of said annular arrangements, and an annular groove formed in an inner wall portion of said second end of the handpiece to receive the other of said annular arrangements.

19. A dental handpiece according to claim 1, in which said annular arrangements are made of solid material.

20. A dental handpiece according to claim 19, in which said arrangements are made of glass or plastics material.

21. A dental handpiece according to claim 1, in which said annular arrangements and said first and second guide portions are all made of the same material.

22. A dental handpiece according to claim 21, in which the material of said annular arrangements and said first and second guide portions blend light transmissively.

23. A dental handpiece according to claim 1, in which said first and second guide portions each comprise a bundle of fibre-optic light guide filaments, said bundles being bent at said second end of the first guide portion and at said first end of the second guide portion so as to form the respective said annular arrangements.

24. A dental handpiece according to claim 3, in which said first and second guide portions each comprise a bundle of fibre-optic light guide filaments arranged to terminate in said annular arrangements, the ends of the filaments in one annular arrangement extending generally parallel to the axis thereof and towards the ends of the filaments in the other annular arrangement.

25. A dental handpiece according to claim 4, in which said first and second guide portions each comprise a bundle of fibre optic light guide filaments arranged to terminate in said annular arrangements, the ends of the filaments in one of said annular arrangements extending radially of the axis thereof and towards the ends of the filaments in the other of the annular arrangements.

26. A dental handpiece according to claim 23, in which said filament ends are fixed in position so as to form the respective said annular arrangements.

27. A dental handpiece arroding to claim 26, in which said filament ends are fixed in position by adhesive.

28. A dental handpiece according to claim 26, including annular fixing bands arranged to fix said filament ends in position in such a way as to leave open the ends thereof for light transmission between the annular arrangements.

29. A dental handpiece according to claim 28, in which said annular fixing bands are made of light proof material.

* * * * *